United States Patent [19]

Itoh

[11] Patent Number: 5,427,957

[45] Date of Patent: Jun. 27, 1995

[54] METHOD AND APPARATUS FOR MONITORING A GAS OR FINE PARTICLES

[75] Inventor: Hiroyasu Itoh, Shizuoka, Japan

[73] Assignee: Hamamatsu Photonics K.K., Shizuoka, Japan

[21] Appl. No.: 203,474

[22] Filed: Feb. 28, 1994

Related U.S. Application Data

[63] Continuation of Ser. No. 807,505, Dec. 16, 1991, abandoned.

[30] Foreign Application Priority Data

Dec. 21, 1990 [JP] Japan .................. 2-404884

[51] Int. Cl.$^6$ .............. G01N 21/76; G01N 21/00; G01N 17/00
[52] U.S. Cl. .................. 436/172; 436/133; 422/82.08; 73/23.34; 73/865.6; 250/459.1
[58] Field of Search .................. 436/133, 172; 422/82.08; 47/1.01, 1.7, DIG. 6, DIG. 8; 73/23.34, 865.6; 250/459.1

[56] References Cited

U.S. PATENT DOCUMENTS

| | | | |
|---|---|---|---|
| 4,768,390 | 9/1988 | Baker et al. | 73/865.6 |
| 5,014,225 | 5/1991 | Vidaver et al. | 364/550 |
| 5,130,545 | 7/1992 | Lussier | 250/458.1 |
| 5,143,853 | 9/1992 | Walt | 436/501 |

FOREIGN PATENT DOCUMENTS 1135091 11/1968 European Pat. Off. .

OTHER PUBLICATIONS

Ireland et al, "The Relationship Between Carbon Dioxide Fixation and Chlorophyll A Fluorescence During Induction of Photosynthesis in Maize Leaves at Different Temperatures and Carbon Dioxide Concentrations", Planta, 160:550–558, 1984.

"Laser-induced fluorescence of green plants. 1: A technique for the remote detection of plant stress and species differentiation", E. W. Chappelle et al., Applied Optics, vol. 23, No. 1, Jan. 1984.

Primary Examiner—Robert J. Warden
Assistant Examiner—Christopher Y. Kim
Attorney, Agent, or Firm—Finnegan, Henderson, Farabow, Garrett & Dunner

[57] ABSTRACT

A carbon dioxide gas is supplied to a living plant while it is illuminated with excitation light, and resulting fluorescence from the plant is detected. Then, a mixture of a carbon dioxide gas and a gas or fine particles to be monitored is supplied to the same living plant while it is illuminated with the excitation light, and resulting fluorescence from the plant is detected. Differences between temporal variations or wavelength characteristics of fluorescence intensities under the above two conditions are used to identify the gas or fine particles.

3 Claims, 2 Drawing Sheets

METHOD AND APPARATUS FOR MONITORING A GAS OR FINE PARTICLES

This application is a continuation of application Ser. No. 07/807,505, filed Dec. 16, 1991, now abandoned.

BACKGROUND OF THE INVENTION

The present invention relates to a method and apparatus for monitoring a gas and fine particles by means of a living plant.

Various techniques have been proposed in which a living organism is used to detect an odor or the like that is present in the form of a gas of a very small quantity or fine particles. A first technique known today is constructing a high-sensitivity odor sensor using a liposome which is an artificial biomembrane. An example of this technique is described in the issue dated May 11, 1989 of Nikkei Sangyo Shinbun. A second approach is detecting an odor gas by. recording a change in the cell potential of a leaf of a plant when a mixture of an odor gas and a carbon dioxide gas is applied to the plant. An example of this approach is described in "Koryo (Perfumes)", No. 158, June 1988.

The prior art techniques described above have suffered from the disadvantage of requiring complicated procedures. For example, the second approach cannot be implemented without erecting electrodes on a leaf of a living plant.

SUMMARY OF THE INVENTION

An object, therefore, of the present invention is to provide a method and apparatus that can identify an odor or the like that is present in the form of a gas of a very small quantity or fine particles in an easy and reliable manner with high precision.

According to the invention, a method for monitoring a gas or fine particles comprises the steps of:
supplying a carbon dioxide gas to a living plant while illuminating it with excitation light, and detecting first fluorescence emitted from the plant;
supplying a mixture of a carbon dioxide gas and the gas or fine particles to be monitored to the plant while illuminating it with the excitation light, and detecting second fluorescence emitted from the plant; and
comparing results of the detection of the first and second fluorescence to identify the gas or fine particles.

Further, according to the invention, an apparatus for monitoring a gas or fine particles comprises:
means for illuminating a living plant with excitation light;
means for selectively supplying the plant with a carbon dioxide gas or a mixture of a carbon dioxide gas and the gas or fine particles to be monitored; and
means for detecting first fluorescence emitted from the plant while the plant is supplied with the carbon dioxide gas, and for detecting second fluorescence emitted from the plant while the plant is supplied with the mixture of the carbon dioxide gas and the gas or fine particles, a difference between results of the detection of the first and second fluorescence being used to identify the gas or fine particles.

DESCRIPTION OF THE PREFERRED EMBODIMENT

An embodiment of the present invention is described below with reference to the accompanying drawings.

Figure 1:
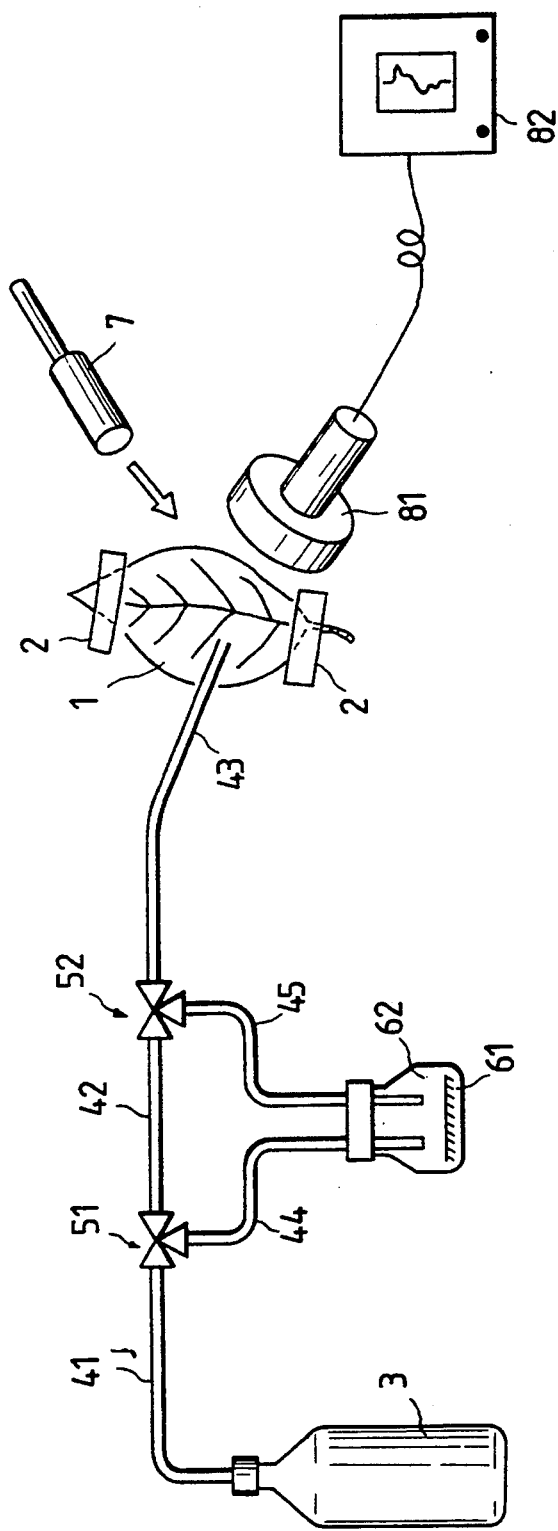
FIG. 1 is a schematic diagram showing the construction of an odor-monitoring system according to an embodiment of the present invention.

FIG. 1 shows the construction of a monitor system according to an embodiment. As shown, a leaf 1 of a living plant is fixed in position by means of tapes 2. A pure carbon dioxide gas in a container 3 is supplied to the leaf 1 via a pipe 41, a three-way valve 51, a pipe 42, a three-way valve 52 and a pipe 43. Other pipes 44 and 45 are connected to the three-way valves 51 and 52, respectively, and a container 62 of an odor substance 61 is provided between these pipes 44 and 45. By controlling the three-way valves 51 and 52, the leaf 1 can selectively be supplied with either a pure carbon dioxide gas or a mixture of a carbon dioxide gas and an odor gas in a desired manner. A light source 7, e.g., a semiconductor laser, is provided for illuminating the leaf 1 with excitation light, and resulting fluorescence is received by a photodiode 81. The output of the photodiode 81 is recorded by a recorder 82.

A monitoring procedure of the system described above is described next.

First, while the leaf 1 is illuminated with the excitation light from the light source 7 and resulting fluorescence is detected by the photodiode 81, a pure carbon dioxide gas is supplied to the leaf 1 from the container 3 via the pipes 41, 42 and 43. A temporal change in the fluorescence intensity and its wavelength characteristic are measured. After a certain period has passed and generation of the fluorescence has returned to the initial state where there was no supply of a carbon dioxide gas, the three-way valves 51 and 52 are switched so that the odor gas in the container 62 is mixed, by a very small quantity, into the carbon dioxide gas being supplied from the container 3. Again, a temporal change in the intensity of resulting fluorescence and its wavelength characteristic are measured. After passage of a given period, the measurement is stopped, and the both measurement results are compared with each other.

Figure 2A:
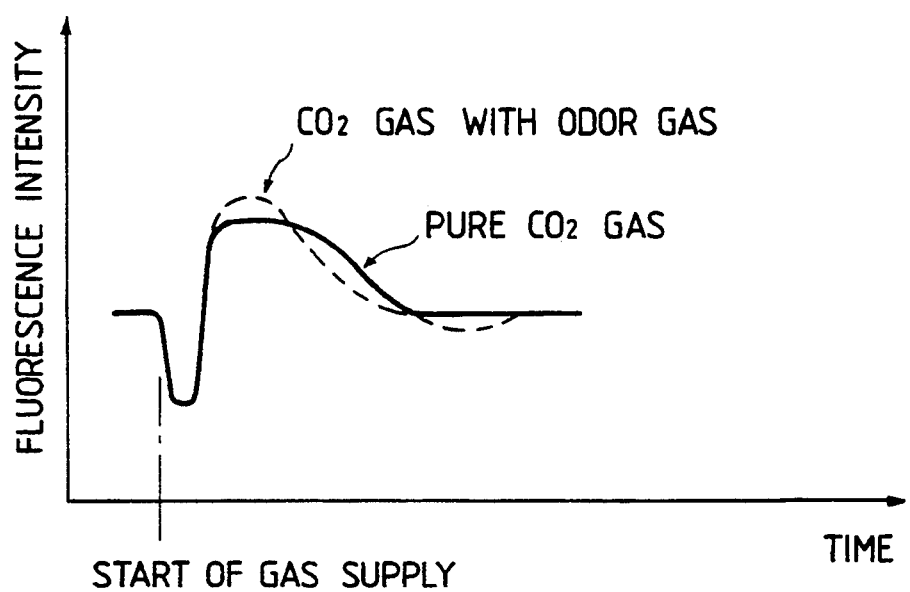
FIG. 2(a) is a graph showing an example of temporal intensity variations of fluorescence emitted from a leaf in response to illumination with excitation light.

FIG. 2(a) shows an example of results of comparison as regards the temporal change in the fluorescence intensity. The solid-line curve represents the case where the pure carbon dioxide gas was supplied, and the dashed-line curve denotes the case of supplying the mixture of the carbon dioxide gas and the odor gas of a very small quantity. In either case, the fluorescence intensity decreases sharply immediately after the supply of a gas, thereafter increases rapidly, and then exhibits a gradual decrease. This intensity variation depends upon whether the odor gas is present or not, and also depends on the amount and kind of odor gas. Further, since the deviation from the case of supplying the pure carbon dioxide gas in the intensity variation curve appears even in the case of supplying a gas of an extremely small quantity (on the ppb order), it is possible to construct a high-sensitivity gas monitor.

Figure 2B:
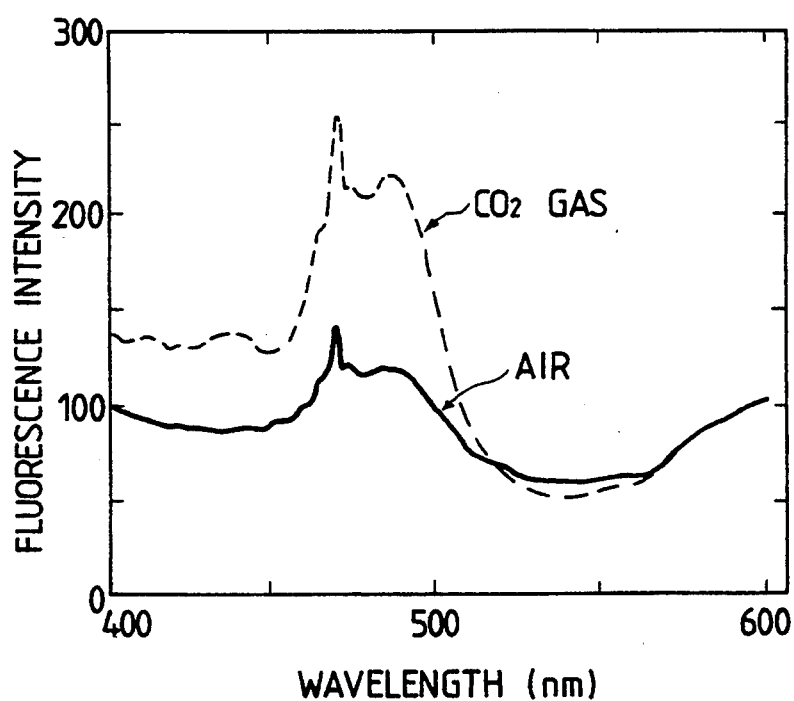
FIG. 2(b) is a graph showing an example of wavelength characteristics of the intensity of fluorescence emitted from the leaf in response to illumination with the excitation light.

FIG. 2(b) shows an example of results of comparison as regards the wavelength dependency of the fluorescence intensity. The solid-line curve represents the case where air was supplied, and the dashed-line curve denotes the case of supplying a carbon dioxide gas. As shown, the presence of the carbon dioxide gas contributes to a significant increase in fluorescence intensity in the wavelength range of less than about 500 nm. In the range of 530–560 nm, the fluorescence intensity is higher in the case of supplying air. Again, since such wavelength dependency of the fluorescence intensity varies with the amount and kind of odor gas or fine particles, it is possible to construct a high-sensitivity gas monitor.

The present invention enables the detection of a gas of an extremely small quantity and, hence, it can be used for the purpose of identifying gases and fine particles that are deleterious to humans, animals or plants. The invention also enables a subject to check the state of his internal organs and other parts by merely breathing out onto a leaf of a monitor plant. The invention also finds utility in checking whether a plant suffers from a disease or insect pests.

As described in the foregoing, in accordance with the present invention, the florescence emitted from a living plant upon illumination with the excitation light while it is supplied with a carbon dioxide gas is detected and compared with the fluorescence emitted from the same living plant upon illumination with the excitation light while it is supplied with a mixture of a carbon dioxide gas and a gas of a very small quantity or fine particles to be monitored. The temporal variation and wavelength characteristic of the fluorescence intensity not only depend on the amount or kind of gas or fine particles to be monitored, but is also responsive to even a gas or fine particles of an extremely small amount. Therefore, results of a comparison between the two cases can be used to monitor the gas or fine particles with high sensitivity, whereby an odor or the like that is present in the form of a gas of a very small quantity or fine particles can be identified in an easy and reliable manner with high precision.

What is claimed is:

1. A method for identifying a specific gas or fine particles from several known gases, comprising the steps of:
   supplying a carbon dioxide gas to a leaf of a living plant while illuminating said leaf with excitation light, and detecting first fluorescence emitted from the leaf;
   supplying a mixture of a carbon dioxide gas and the specific gas or fine particles to be identified to the leaf while illuminating it with the excitation light, and detecting second fluorescence emitted from the leaf; and
   comparing results of the detection of the first and second fluorescence to identify the specific gas or fine particles.

2. The method of claim 1, wherein the step of comparing results of the detection of the first and second fluorescence includes comparing temporal variations of fluorescence intensities.

3. The method of claim 1, wherein the step of comparing results of the detection of the first and second fluorescence includes comparing wavelength characteristics of fluorescence intensities.

* * * * *

UNITED STATES PATENT AND TRADEMARK OFFICE
CERTIFICATE OF CORRECTION

PATENT NO. : 5,427,957
DATED : June 27, 1995
INVENTOR(S) : Hiroyasu Itoh

It is certified that error appears in the above-indentified patent and that said Letters Patent is hereby corrected as shown below:

Column 4,

Claim 1, lines 11-26, delete in its entirety and substitute therefor:

— 1. A method for determining the presence or absence of a predetermined gas or fine particles in a sample, comprising the steps of:

supplying a carbon dioxide gas to a leaf of a living plant while illuminating said leaf with excitation light, and detecting first fluorescence emitted from the leaf;

supplying a sample gas containing carbon dioxide gas to the leaf while illuminating it with the excitation light, and detecting the second fluorescence emitted from the leaf; and comparing results of the detection of the first and second fluorescence to determine the presence or absence of the gas or fine particles in the sample gas.—

Signed and Sealed this

Tenth Day of September, 1996

Attest:

BRUCE LEHMAN

*Attesting Officer*    *Commissioner of Patents and Trademarks*